US010595849B2

(12) United States Patent
Kaplan

(10) Patent No.: US 10,595,849 B2
(45) Date of Patent: Mar. 24, 2020

(54) SURGICAL INSTRUMENTS

(71) Applicant: Lee D. Kaplan, Coconut Grove, FL (US)

(72) Inventor: Lee D. Kaplan, Coconut Grove, FL (US)

(*) Notice: Subject to any disclaimer, the term of this patent is extended or adjusted under 35 U.S.C. 154(b) by 158 days.

(21) Appl. No.: 15/669,496

(22) Filed: Aug. 4, 2017

(65) Prior Publication Data
US 2017/0333028 A1    Nov. 23, 2017

Related U.S. Application Data

(63) Continuation of application No. 13/486,584, filed on Jun. 1, 2012, now Pat. No. 9,757,112, which is a continuation of application No. 12/102,260, filed on Apr. 14, 2008, now Pat. No. 8,202,295, which is a
(Continued)

(51) Int. Cl.
A61B 17/04    (2006.01)
A61B 17/06    (2006.01)

(52) U.S. Cl.
CPC ...... *A61B 17/0401* (2013.01); *A61B 17/0487* (2013.01); *A61B 17/06166* (2013.01); *A61B 2017/045* (2013.01); *A61B 2017/0409* (2013.01); *A61B 2017/0414* (2013.01); *A61B 2017/0446* (2013.01); *A61B 2017/0496* (2013.01); *Y10T 24/3967* (2015.01)

(58) Field of Classification Search
CPC ............ A61B 17/0401; A61B 17/0487; A61B 17/06166; A61B 2017/0409; A61B 2017/0446; A61B 2017/0414; A61B 2017/0496; A61B 2017/045; Y10T 24/3967
See application file for complete search history.

(56) References Cited

U.S. PATENT DOCUMENTS 254,473 A      3/1882  Gates
306,078 A *   10/1884  Hubner ................... A62B 1/14
                                                              182/7
(Continued)

FOREIGN PATENT DOCUMENTS

EP    1 486 171    12/2004
JP    11-506644     6/1999
(Continued)

OTHER PUBLICATIONS

Examiner's Report received for Australian Appln. No. 2007275351 dated Feb. 8, 2012.
(Continued)

*Primary Examiner* — Phong Son H Dang
(74) *Attorney, Agent, or Firm* — Foley & Lardner LLP

(57) ABSTRACT

A surgical instrument having an anchor and a plug is capable of anchoring a suture. The suture anchor has an anchor body having a top surface, a bottom surface distal to the top surface, a transverse bore and a well, the well having an outer surface, an inner surface, and an inner bottom surface. The plug has a post, a head, and a bottom face. The anchor body and the anchor plus form a suture anchor. The suture anchor may be used during surgical procedures and can be used in the re-tensioning of a suture.

23 Claims, 7 Drawing Sheets

Related U.S. Application Data continuation-in-part of application No. 11/778,951, filed on Jul. 17, 2007, now abandoned.

(60) Provisional application No. 60/832,035, filed on Jul. 20, 2006, provisional application No. 60/832,253, filed on Jul. 20, 2006, provisional application No. 60/832,289, filed on Jul. 20, 2006.

(56) References Cited

U.S. PATENT DOCUMENTS

| | | | |
|---|---|---|---|
| 1,993,391 A * | 3/1935 | Weaver, Jr. | H01R 4/32 24/135 R |
| 2,429,448 A | 10/1947 | Bakke | |
| 2,907,978 A * | 10/1959 | Bergan | H01R 4/363 439/793 |
| 3,268,965 A | 8/1966 | Arthur | |
| 3,923,406 A * | 12/1975 | Iritz | F16G 11/06 24/135 R |
| 3,962,091 A * | 6/1976 | Doria | B01D 33/067 210/232 |
| 4,213,669 A * | 7/1980 | Wittes | H01R 4/36 439/811 |
| 4,259,072 A * | 3/1981 | Hirabayashi | A61C 8/0012 433/173 |
| 4,427,258 A * | 1/1984 | Mueller | H01R 4/36 439/488 |
| 4,623,338 A * | 11/1986 | Larson | A61F 5/4404 24/135 N |
| 4,750,492 A | 6/1988 | Jacobs | |
| 4,870,957 A | 10/1989 | Goble et al. | |
| 4,927,421 A | 5/1990 | Goble et al. | |
| 5,037,422 A | 8/1991 | Hayhurst et al. | |
| 5,152,790 A | 10/1992 | Rosenberg et al. | |
| 5,156,616 A | 10/1992 | Meadows et al. | |
| 5,176,682 A | 1/1993 | Chow | |
| 5,268,001 A | 12/1993 | Nicholson et al. | |
| 5,356,435 A | 10/1994 | Thein | |
| 5,370,662 A | 12/1994 | Stone et al. | |
| 5,376,119 A | 12/1994 | Zimmermann et al. | |
| 5,383,905 A | 1/1995 | Golds et al. | |
| 5,423,860 A | 6/1995 | Lizardi et al. | |
| 5,458,601 A | 10/1995 | Young et al. | |
| 5,464,427 A | 11/1995 | Curtis et al. | |
| 5,480,403 A | 1/1996 | Lee et al. | |
| 5,486,197 A | 1/1996 | Le et al. | |
| 5,527,342 A | 6/1996 | Pietrzak et al. | |
| 5,545,180 A | 8/1996 | Le et al. | |
| 5,584,835 A | 12/1996 | Greenfield | |
| 5,630,824 A | 5/1997 | Hart | |
| 5,690,676 A | 11/1997 | Dipoto et al. | |
| 5,702,397 A | 12/1997 | Goble et al. | |
| 5,720,765 A | 2/1998 | Thal | |
| 5,723,013 A | 3/1998 | Jeanson et al. | |
| 5,725,529 A | 3/1998 | Nicholson et al. | |
| 5,728,136 A | 3/1998 | Thal | |
| 5,733,307 A | 3/1998 | Dinsdale | |
| 5,797,963 A | 8/1998 | McDevitt | |
| 5,911,721 A | 6/1999 | Nicholson et al. | |
| 5,929,383 A * | 7/1999 | Marik | H02G 15/04 174/78 |
| RE36,289 E | 8/1999 | Le et al. | |
| 5,935,129 A | 8/1999 | McDevitt et al. | |
| 5,948,000 A | 9/1999 | Larsen et al. | |
| 5,948,001 A | 9/1999 | Larsen | |
| 5,957,953 A | 9/1999 | Dipoto et al. | |
| 6,086,608 A | 7/2000 | Ek et al. | |
| 6,117,162 A | 9/2000 | Schmieding et al. | |
| 6,136,032 A | 10/2000 | Viladot Perice et al. | |
| 6,149,669 A | 11/2000 | Li | |
| 6,159,235 A | 12/2000 | Kim | |
| 6,200,329 B1 | 3/2001 | Fung et al. | |
| 6,200,330 B1 | 3/2001 | Benderev et al. | |
| 6,267,766 B1 | 7/2001 | Burkhart | |
| 6,319,271 B1 | 11/2001 | Schwartz et al. | |
| 6,368,326 B1 | 4/2002 | Dakin et al. | |
| 6,436,124 B1 | 8/2002 | Anderson et al. | |
| 6,436,142 B1 | 8/2002 | Paes et al. | |
| RE37,963 E | 1/2003 | Thal Raymond | |
| 6,520,980 B1 | 2/2003 | Foerster | |
| 6,527,794 B1 | 3/2003 | McDevitt et al. | |
| 6,532,711 B2 * | 3/2003 | Gregel | E04C 5/165 52/583.1 |
| 6,533,816 B2 | 3/2003 | Sklar | |
| 6,575,987 B2 | 6/2003 | Gellman et al. | |
| 6,585,730 B1 | 7/2003 | Foerster | |
| 6,616,694 B1 | 9/2003 | Hart | |
| 6,641,596 B1 | 11/2003 | Lizardi | |
| 6,652,563 B2 | 11/2003 | Dreyfuss | |
| 6,692,516 B2 | 2/2004 | West et al. | |
| 6,736,829 B1 | 5/2004 | Li et al. | |
| 6,840,953 B2 | 1/2005 | Martinek | |
| 7,074,203 B1 * | 7/2006 | Johanson | A61F 2/0805 411/34 |
| 7,083,638 B2 | 8/2006 | Foerster | |
| 7,090,690 B2 | 8/2006 | Foerster et al. | |
| 7,416,556 B2 | 8/2008 | Jackson | |
| 7,491,217 B1 * | 2/2009 | Hendren | A61B 17/0401 606/232 |
| 7,517,357 B2 | 4/2009 | Abrams et al. | |
| 7,585,311 B2 | 9/2009 | Green et al. | |
| 7,938,847 B2 | 5/2011 | Fanton et al. | |
| 8,118,835 B2 | 2/2012 | Weisel et al. | |
| 8,133,258 B2 | 3/2012 | Foerster et al. | |
| 8,137,381 B2 | 3/2012 | Foerster et al. | |
| 8,162,978 B2 | 4/2012 | Lombardo et al. | |
| 2002/0147463 A1 | 10/2002 | Martinek | |
| 2003/0065361 A1 | 4/2003 | Dreyfuss | |
| 2003/0083669 A1 | 5/2003 | Gleason | |
| 2003/0195563 A1 | 10/2003 | Foerster | |
| 2004/0088004 A1 | 5/2004 | Rosch | |
| 2004/0093031 A1 | 5/2004 | Burkhart et al. | |
| 2004/0098050 A1 | 5/2004 | Foerster et al. | |
| 2004/0098052 A1 | 5/2004 | West et al. | |
| 2004/0138706 A1 | 7/2004 | Abrams et al. | |
| 2004/0138707 A1 | 7/2004 | Greenhalgh | |
| 2005/0055052 A1 | 3/2005 | Lombardo et al. | |
| 2005/0222618 A1 | 10/2005 | Dreyfuss et al. | |
| 2005/0245932 A1 | 11/2005 | Fanton et al. | |
| 2006/0253119 A1 | 11/2006 | Berberich et al. | |
| 2006/0271060 A1 | 11/2006 | Gordon | |
| 2007/0005068 A1 * | 1/2007 | Sklar | A61B 17/0401 606/139 |
| 2007/0203498 A1 | 8/2007 | Gerber et al. | |
| 2008/0033460 A1 | 2/2008 | Ziniti et al. | |
| 2008/0051836 A1 | 2/2008 | Foerster et al. | |
| 2008/0077161 A1 | 3/2008 | Kaplan | |
| 2009/0112270 A1 | 4/2009 | Lunn et al. | |
| 2004/0312794 | 12/2009 | Nason et al. | |
| 2009/0312794 A1 | 12/2009 | Nason et al. | |
| 2010/0004683 A1 * | 1/2010 | Hoof | A61B 17/0401 606/232 |
| 2010/0318125 A1 * | 12/2010 | Gerber | A61B 17/0401 606/232 |

FOREIGN PATENT DOCUMENTS

| | | |
|---|---|---|
| JP | 2003-505128 | 2/2003 |
| JP | 2003-528648 | 9/2003 |
| JP | 2007-532269 | 11/2007 |
| WO | WO-96/39082 | 12/1996 |
| WO | WO-97/29693 | 8/1997 |
| WO | WO-98/35606 | 8/1998 |
| WO | WO-01/06909 | 2/2001 |
| WO | WO-01/10312 | 2/2001 |

(56) References Cited

FOREIGN PATENT DOCUMENTS

| WO | WO-02/38059 | 5/2002 |
|---|---|---|
| WO | WO-2006/060035 | 6/2006 |

OTHER PUBLICATIONS

Extended European Search Report in EP Application No. 09755517.1 dated Jan. 14, 2015 (6 pages).
Final Office Action in U.S. Appl. No. 12/885,201 dated May 30, 2014 (15 pages).
Final Office Action in U.S. Appl. No. 13/486,584 dated Aug. 21, 2013.
Final Office Action in U.S. Appl. No. 13/486,584 dated Jun. 30, 2016 (16 pages).
Final Office Action issued on U.S. Appl. No. 13/413,501, dated Sep. 17, 2012.
Final Office Action on U.S. Appl. No. 12/885,201, dated Sep. 24, 2012.
Final Office Action received for U.S. Appl. No. 11/778,951 dated Jul. 10, 2009.
Final Office Action received for U.S. Appl. No. 11/778,951 dated Jul. 20, 2010.
Final Office Action recieved for U.S. Appl. No. 12/102,260 dated May 6, 2011.
International Preliminary Report on Patentability received for PCT/US2009/039787 dated Oct. 26, 2010.
International Search Report and Written Opinion for PCT/US07/73697 dated Sep. 8, 2008.
International Search Report and Written Opinion for PCT/US09/39787 dated May 14, 2009.
Non-Final Office Action in U.S. Appl. No. 12/885,201 dated Nov. 26, 2013 (11 pages).
Non-Final Office Action in U.S. Appl. No. 13/486,584 dated Feb. 19, 2014 (6 pages).
Non-Final Office Action in U.S. Appl. No. 13/486,584 dated Mar. 12, 2015 (12 pages).
Non-Final Office Action in U.S. Appl. No. 13/486,584 dated Oct. 8, 2015 (15 pages).
Non-Final Office Action in U.S. Appl. No. 13/486,584 dated Aug. 1, 2014 (8 pages).
Non-Final Office Action issued in U.S. Appl. No. 13/413,501 and dated Jun. 1, 2012.
Non-Final Office Action issued on U.S. Appl. No. 13/486,411, dated Nov. 27, 2012.
Non-Final Office Action issued on U.S. Appl. No. 13/486,584, dated Oct. 31, 2012.
Non-Final Office Action issued on U.S. Appl. No. 12/885,201, dated Oct. 31, 2012.
Non-final Office Action received for U.S. Appl. No. 11/778,951 dated Jan. 12, 2010.
Non-final Office Action received for U.S. Appl. No. 11/778,951 dated Jan. 13, 2009.
Non-final Office Action received for U.S. Appl. No. 12/102,260 dated Nov. 26, 2010.
Non-final Office Action received for U.S. Appl. No. 12/885,201 dated Apr. 25, 2012.
Notice of Allowance (2nd) received for U.S. Appl. No. 12/102,260; dated Mar. 26, 2012.
Notice of Allowance in U.S. Appl. No. 13/486,411 dated Aug. 19, 2013.
Notice of Allowance in U.S. Appl. No. 13/486,584 dated May 8, 2017 (8 pages).
Notice of Allowance issued for U.S. Appl. No. 13/413,501 dated Nov. 30, 2012.
Notice of Allowance issued in U.S. Appl. No. 13/413,501 dated Jan. 25, 2013.
Notification of Reason for Rejection in Japanese application No. 2011-504128 dated Nov. 5, 2013 (English translation—2 pages).
Notification of Reason for Rejection Received for Japanese Appln. No. 2009-520957 dated Mar. 5, 2012.
Office Action in Japanese Application No. 2009-52957 dated Dec. 10, 2012. (English Translation Only).
Office Action in Japanese Application No. 2011-504128 dated Jun. 12, 2013 (English translation).
Office Action issued in Japanese Application No. 2013-092993 dated Mar. 19, 2014 (3 pages—English translation unavailable).
Patent Examination Report No. 1 in Australian application No. 2009251530 dated Oct. 25, 2013 (3 pages).
Patent Examination Report No. 2 Issued in Australian Patent Application No. 2007275351 dated Jul. 31, 2013.

* cited by examiner

SURGICAL INSTRUMENTS

CROSS-REFERENCE TO RELATED APPLICATIONS

This application is a continuation of U.S. patent application Ser. No. 13/486,584, filed on Jun. 1, 2012, which is a continuation of U.S. patent application Ser. No. 12/102,260, filed on Apr. 14, 2008, having issued as U.S. Pat. No. 8,202,295 on Jun. 19, 2012, which is a continuation-in-part of U.S. patent application Ser. No. 11/778,951, filed on Jul. 17, 2007, which in turn claims the benefit of U.S. Provisional Applications 60/832,035, 60/832,253 and 60/832,289, all of which were filed on Jul. 20, 2006, and all of the above applications are hereby incorporated by reference, in their entirety, for any and all purposes.

FIELD

The present disclosure generally related to surgical instruments. More specifically, the disclosure relates to a suture anchor.

BACKGROUND

Suture anchors are well known in the art. Suture anchors are typically used to anchor soft tissues such as tendons, and the like, to bone using a suture. The suture anchor is typically secured in a bone and sutures, previously having been inserted into tissue, are then threaded through the suture anchor to tension the tissue and hold it in place. The tissue is tensioned to the bone via the suture attached to the anchor.

Typically, the suture is threaded through a small hole, or series of holes in the anchor and some suture anchors come pre-loaded with the sutures. The suture can then be knotted to prevent release of the suture from the suture anchor. However, the need for knotting can increase surgical time and provide a weak point for suture breakage, hence a need exists for a suture anchor that is fast to use, readily allows for re-tensioning of a suture, and does not introduce knotting weakness to the suture.

Surgical cannulas are used to enter areas within the body such as the shoulder, knee, or abdomen. The cannula provides a means for passing surgical instruments into and out of a subject. Cannulas are also used as a channel to introduce surgical implements such as surgical instruments, suture anchors, or sutures. Such surgical cannulas typically have a single chamber that is conducive to instruments or items touching and either cross-contaminating one another or disturbing the function of each other. Such surgical cannulas are also subject to the cannula readily pulling out of the subject or falling into a subject and requiring re-insertion or extraction. A need exists for cannulas that resist the tendency to push out of a subject, or fall into a subject. Also multi-chambered cannulas are desired.

SUMMARY

In a first aspect, a surgical instrument is provided comprising (a) an anchor comprising (i) a wall comprising (1) an outer surface having threads; and (2) an inner surface; (iii) a first end; and a second end; and (b) a plug comprising a first end, a second end, and an outer wall; wherein the anchor and the plug form a suture anchor capable of anchoring a suture.

In one embodiment, the outer wall of the plug comprises threads capable of engaging the inner surface of the anchor via a friction fit. In another embodiment, the inner surface comprises threads. In another embodiment, the outer wall of the plug and the inner wall of the anchor each have threads capable of engaging each other in a screw-like fashion to secure the plug in the anchor.

In another embodiment, the plug is made of a compressible material. For example, the compressible material may be a polymer such as high density polyethylene, polyurethane, silicones, or a mixture thereof.

In some embodiments, the first end of the plug has the same diameter as the second end of the plug. In other embodiments, the first end of the plug has a larger diameter than the second end of the plug, such that the plug forms conical shape similar to that of the profile of a funnel.

In another aspect, methods of using a suture anchor is provided comprising: securing the anchor into a bone, draping a suture through an interior of the anchor and touching the inner surface; and inserting the plug in the anchor to secure and tension the suture. In some embodiments, the securing is via screwing or cementing of the anchor in the bone. Other embodiments, further comprise removing the plug; re-tensioning the suture; and replacing the plug in the anchor.

In another aspect, a suture anchor has an anchor body that has a well, a top surface, a bottom surface, and a transverse bore. The well has an outer surface, an inner surface, and an inner bottom surface. In such embodiments, the anchor and the plug form a suture anchor configured to secure a surgical suture. In some embodiments, the transverse bore is proximally located to the inner bottom surface. In some embodiments, grooves are formed in the outer surface extending from the transverse bore to the top surface. In other embodiments, the outer surface has rungs and the inner surface has threads. In other embodiments, the post is a threaded post.

In some embodiments, the outer surface has rungs, the inner surface has, the post is a threaded post, and the threads of the inner surface and the threads of the post are configured to engage in a screw-like fashion to secure the anchor plug in the anchor body.

Methods of using such a suture anchor are also provided. Such methods include boring a nest in a bone; positioning the bottom surface of the anchor body in the nest; threading a suture through the transverse bore; driving the suture anchor into the nest; tensioning the suture; and securing the suture in the anchor body with the anchor plug. Alternatively, the threading of the suture precedes the positioning of the anchor body in the nest. In some embodiments, the methods also include loosening or removing the anchor plug, re-tensioning the suture, and tightening or replacing the anchor plug in the anchor body.

In another aspect, surgical instrument is provided comprising (a) a cannula comprising a distal end, a proximal end and at least one chamber extending the entire length of the cannula from the proximal end to the distal end; (b) at least one inflatable donut; and (c) an air passageway having an air inlet; wherein the inflatable donut has a circumference at full inflation that is greater than a circumference of the cannula. In some embodiments, the cannula is capable of passing a surgical item into and out of a subject undergoing surgery. For example, surgical items include, but are not limited to, surgical instruments, sutures, and implants.

In some embodiments, the cannula comprises a divider that divides the at least one chamber extending the entire length of the cannula into at least two chambers. In some embodiments, the divider is a flexible diaphragm or divider. In other embodiments, the divider extends the full length of the cannula.

In other embodiments, the cannula further comprises a second donut. In some such embodiments, the second donut is rigid or inflatable. In other embodiments, the second donut is capable of preventing insertion of the cannula completely into a subject. In yet other embodiments, the second donut is formed integrally with the cannula. In yet other embodiments, the second donut is formed separately from the cannula and is attached to the cannula.

In other embodiments of the cannula, the inflatable donut is capable of being inflated via the air passageway. In some embodiments, a pump is used to inflate the inflatable donut via the air passageway. In other embodiments, an air-filled syringe inserted through a valve is used to inflate the inflatable donut via the air passageway.

In another aspect, a method of using the cannula is provided comprising: making an incision in the subject at the location in which the cannula is to be inserted; inserting the cannula; and inflating the at least one inflatable donut. In other embodiments, the method further comprises: conducting a surgical procedure using the cannula; deflating the inflatable donut; and removing the cannula from the subject.

DESCRIPTION

Figure 1:
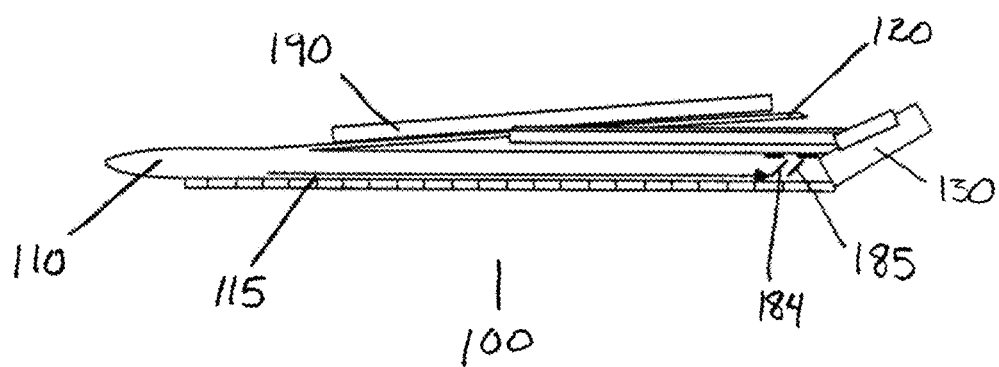
FIG. 1 is a side view of a suture passer without a suture.
Figure 2:
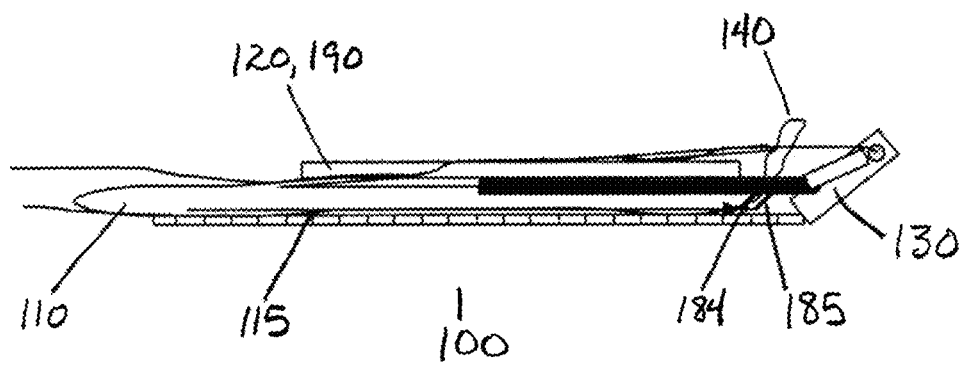
FIG. 2 is a side view of a suture passer having a suture threaded through the suture passer.
Figure 3:
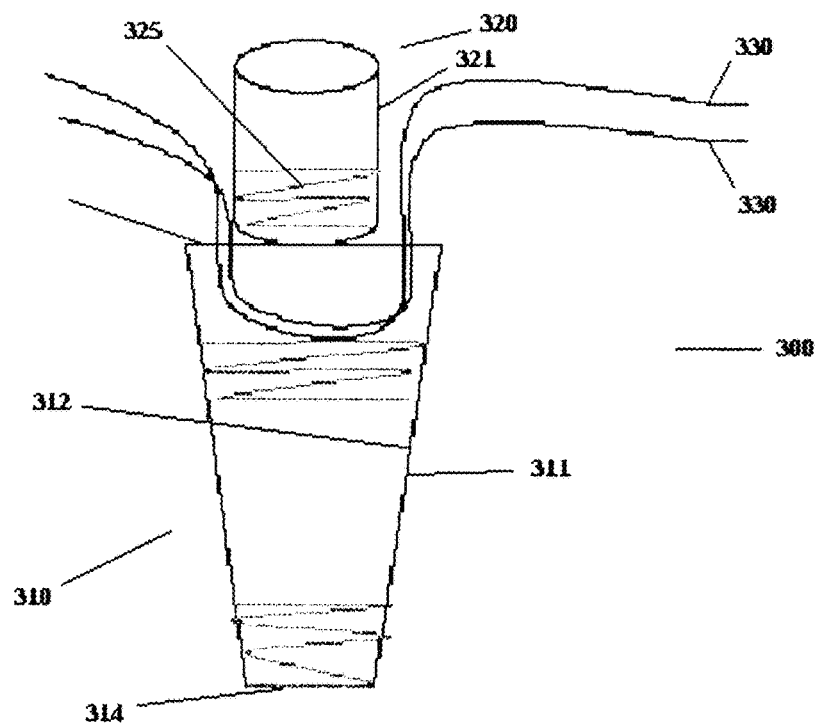
FIG. 3 is a side view of a suture anchor showing the plug and the nest with a sutures passing through, prior to insertion of the plug into the nest.
Figure 4:
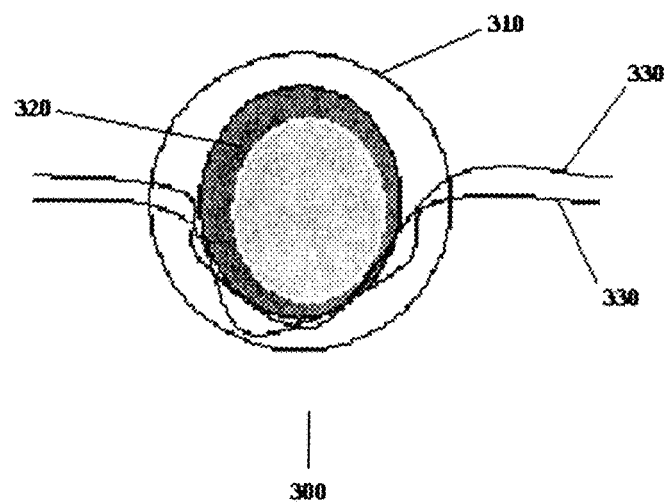
FIG. 4 is a top view of a suture anchor showing the plug and the nest with a sutures passing through, prior to insertion of the plug into the nest.
Figure 5:
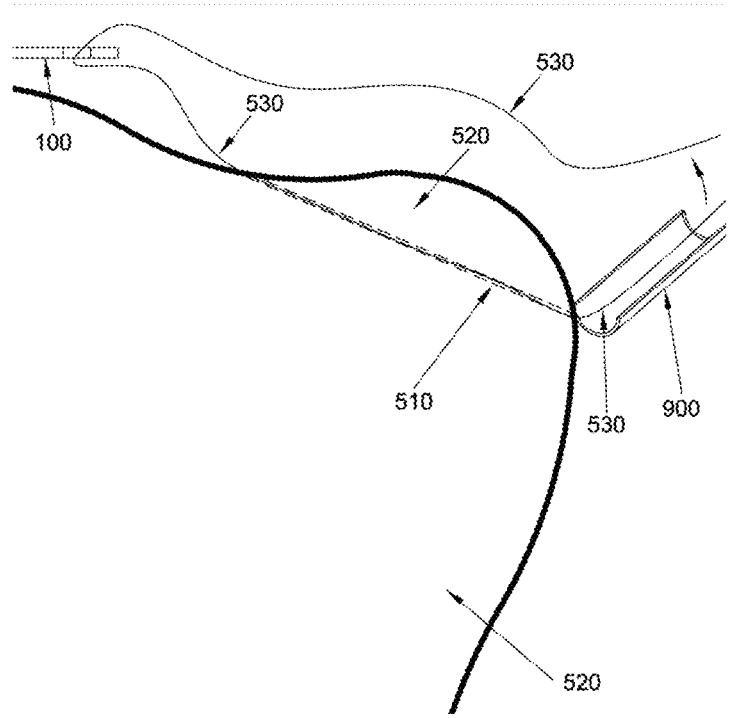
FIG. 5 is an illustration of a humerus with a hole bored through a portion for the passage of a suture to secure a rotator cuff bed.
Figure 6:
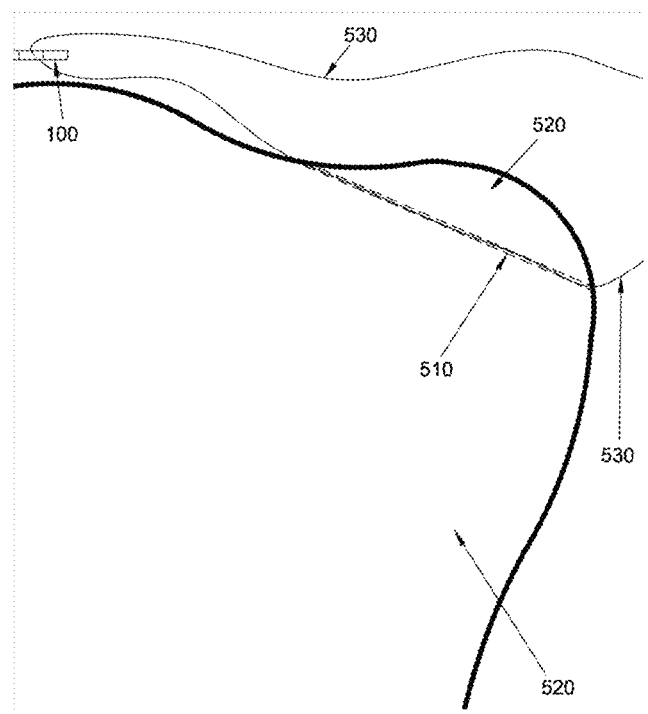
FIG. 6 is an illustration of a humerus with a hole bored through a portion for the passage of a suture to secure a rotator cuff bed.
Figure 7:
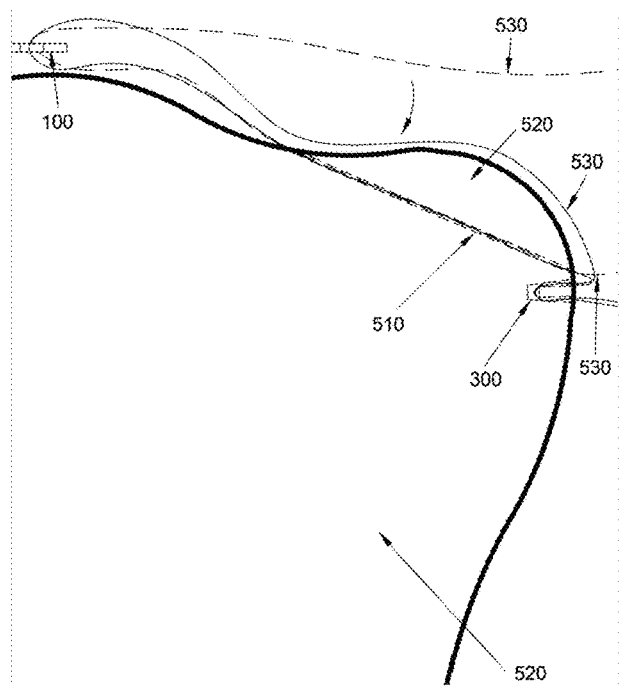
FIG. 7 is an illustration of a humerus with a hole bored through a portion for the passage of a suture to secure a rotator cuff bed and a suture anchor secured in the humerus.
Figure 8:
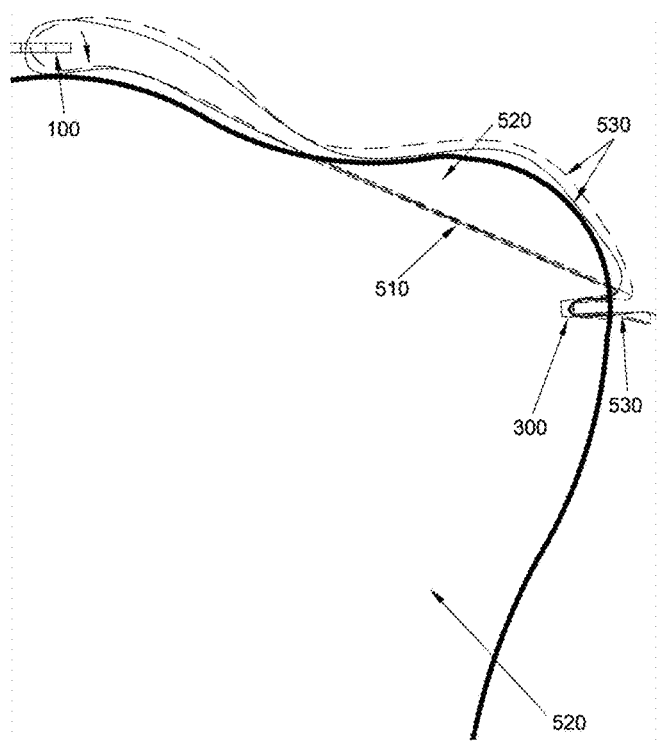
FIG. 8 is an illustration of a humerus with a hole bored through a portion for the passage of a suture to secure a rotator cuff bed and a suture anchor secured in the humerus with the suture beginning to be tensioned.

In one aspect, an instrument comprising a suture passer 100 is described. As shown in FIGS. 1 and 2, the suture passer 100 comprises a body 110 having a tunnel 115, an articulating arm 120, 190 connected to the body 110 proximally to a first end of the body 110, and a fore end 130 distal to the first end of the body 110. In some embodiments, the suture passer 100, further comprises suture channels 184, 185 through which sutures are threaded to load the suture passer 100. In some embodiments, the suture passer 100 is an arthroscopic instrument. The suture passer 100 may be used to grasp tissue and pass a sliding, locking suture in a single grasp of the tissue. The suture passer 100 grasps tissue 180 between the body 110 and the articulating arm 120. The suture passer 100 then passes a suture loop 140 through the tissue 180. This may be done by loading the suture 140 in a U fashion. A needle passes through the tunnel 115 then penetrates the tissue 180 passing through the suture loop 140. A second needle or a pass of the same needle passes through a channel within articulating arm 120 and is directed through the suture loop 140 and capturing the other end of the suture. This pulls one end of the suture back in a retrograde fashion through the first loop 140 creating a locking stitch. The suture has one end outside the body 110 and the other end loaded on the other side of the suture passer 100. This allows for it to be passed through the suture loop 140, ultimately forming a locking stitch. One end of the suture is passed below the tissue 180 and one end is passed above the tissue 180. When the bottom suture is pulled longitudinally it pulls the suture loop 140 down perpendicular to the tissue 180 resulting in bringing it downward. When the top suture is pulled it brings the tissue 180 laterally or in line with the sutures. In one embodiment, the articulating arm 120 is connected to the body 110 by a joint or a hinge, such that the articulating arm 120 may move relative to the body 110 in a tweezer-like fashion.

In other embodiments, the suture passer 100 will grasp tissue, thus allowing for a loop of a single suture (or multiple sutures) to be placed from an inferior aspect of the tissue to a superior aspect of the tissue. A needle or grasping agent will then reach through this loop and pull the other end of the suture back through this suture loop. This will create a locking stitch with one end on the superior and one end on the inferior aspect of the tissue. This is accomplished by a needle driving the loop of suture through the tissue. This needle passes through a channel in the inferior arm of the suture passer. The second needle or grasping agent penetration runs parallel to the first but on the other side of the tissue. This needle may be have passage through the superior arm of the suture passer. This allows it to be on the other side of the tissue as the first arm or inferior arm and on the same side as the suture loop. Thus, going through the loop and pulling back the other end of suture. The result is a locking stitch with suture limbs on both sides of the tissue.

While conventional suture anchors known to those of skill in the art may be used to secure sutures required for tissue repair using the suture passer 100 described above, in another aspect, a suture anchor 300 comprising an anchor 310, and a plug 320 is described herein and is illustrated in FIGS. 3-8. Such suture anchors 300 may be used with the suture passers 100, described above, or the suture anchors 300 may be used in any suturing application known to those of skill in the art.

Suture anchors 300 embodied herein, allow for one or more points of fixation of a tissue to be anchored by a single anchor position. As described below, the suture anchors embodied herein are capable allowing the tensioning of a tissue with a suture to be adjustable and re-tensionable.

Referring to FIGS. 3-8, the anchor 310 comprises a wall having an outer surface 311, an inner surface 312, that may or may not have threads to secure the plug 320, a first end 313, and a second end 314. In the either case of the inner surface 312, having or not having threads, it is a friction fit between the plug 320 and the inner surface 312 that secures the plug 320 into the suture anchor 300. In some cases, a diameter of the first end 313 is larger than a diameter of the second end 314, while in other embodiments, the first end 313 and the second end 314 have the same diameter. The plug 320 comprises an outer wall 321 having threads 325 such that when a suture(s) 330 is draped into the anchor 310 and the plug 320 is inserted into the anchor 310, the plug 320 secures the suture(s) 330 via a friction fit between the plug 320 and the inner surface 312 of the wall 311. FIGS. 5-8 further illustrate the suture anchor 300 secured in a humerus 510 and with sutures 530 anchored in the suture anchor 300.

Anchor 310 may be secured in any bone via a screw mechanism on the outer surface 311 of the wall, or via a cementing of the anchor 310 to the bone, as is known to those of skill in the art. The anchor 310 may also have a means for driving the screw mechanism into bone. For example, the anchor 310 may have a hex-head, slot, Phillips-type head, or other shaped head that may be mated to a driver for screwing the anchor 310 into bone. Cementing of the anchor 310 to the bone may be accomplished using a variety of bone cements known to those of skill in the art. For example, curable polymers such as polymethylmethacrylate may be used.

Such suture anchors 300 allow for tightening, adjustment, or re-tensioning of a suture by loosening and/or removal of the plug 320 from anchor 310, adjusting or re-tensioning of the suture, and tightening and/or re-insertion of the plug 320 into the anchor 310. Such suture anchors 300 also allow for securing of the suture without the tying of knots or replacement of sutures when re-tensioning is required. Suture anchors 300 may be used for the fixation of soft tissue to bone, or of bone to bone.

Suture anchors 300 and plugs 320 may be made from a variety of materials known to those of skill in the art. For example, for the suture anchors 300 the material is typically a rigid material such as a metal, a polymer, or a ceramic. Biocompatible metals include, but are not limited to stainless steel, titanium, tantalum, aluminum, chromium, molybdenum, cobalt, silver, and gold, or alloys of such metals that are known to those of skill in the art. Biocompatible polymers include, but are not limited to, high-density polyethylenes, polyurethanes, or blends of such polymers, as are known to those of skill in the art. Biocompatible polymers also include absorbable materials such as polylactic acid, polyglycolic acid, or mixtures thereof. Biocompatible ceramics include, but are not limited to alumina, silica, silicon carbide, silicon nitride, zirconia, and mixtures of any two or more thereof.

The plugs 320 may likewise be prepared from similar metals, polymers, and ceramics, however in some embodiments, the plugs 320 are prepared from materials that may be compressed. In such embodiments, the plug material is capable of being compressed from an uncompressed state to a compressed state, prior to or during insertion of the plug 320 into the suture anchor 300. Such compression allows for the material to recoil from the compressed state to the uncompressed state and thereby increasing the friction fit between the plug 320 and the suture anchor 300. Such materials that may be compressed include, but are not limited to, polyethylenes, silicones, polyesters, polyurethanes, polylactic acid, polyglycolic acid, or mixtures of any two or more thereof.

The anchor 300 may be used to secure sutures tensioning tissue without tissue to bone direct contact. Examples of such uses of suture tensioning without tissue to bone contact include, but are not limited to, pelvic surgery, bladder suspension surgery, brow lift or face lift surgery, hand surgery and the like.

Suture anchors 1000 are also embodied herein, and allow for one or more points of fixation of a tissue to be anchored by a single anchor position. As described below, the suture anchors embodied herein are capable allowing the tensioning of a tissue with a suture to be adjustable, and re-tensionable.

Referring to FIGS. 10-13, the anchor 1000 comprises an anchor body 1010 and a plug 1020. The anchor body 1010 has a central region, or well, that is bored out to accept the anchor plug 1020. The well is surrounded by a wall having an outer surface 1017, an inner surface 1018, and a top surface 1016. The well also has a bottom inner surface (i.e. the bottom of the well), and a bottom outer surface (i.e. the bottom of the anchor body 1010). The inner surface 1018 of the anchor body 1010 may have threads 1015 to accept corresponding threads 1023 on the anchor plug 1020. The top edge of the inner surface 1018 of the wall, proximal to the top surface 1016, may have a bevel 1019. The outer surface 1017 of the wall may have rungs or ridges 1014 for securing the plug 1020 in bone or other tissue. The rungs or ridges 1014 provide anchoring ability to the anchor body 1010 and the suture anchor 1000 as a whole to prevent either from readily pulling out of the bone or other tissue when tensioning a suture, or over the time of implantation in a subject. Alternatively, the bored central region of the anchor body 1010 may not be threaded, but is a smooth bore that can accept an anchor plug via a friction fit. The anchor body 1010 may accommodate sutures that are draped into the anchor body 1010, and a friction fit anchor plug is then inserted, or the anchor body 1010 may accommodate sutures that are threaded through a transverse bore 1012 in the anchor body 1010, to be secured in place by an anchor plug 1020.

The transverse bore 1012 in the anchor body 1010 is capable of receiving one or more sutures to be secured by the suture anchor 1000. The transverse bore 1012 is configured proximally to the bottom of the well, such that a suture may be secured between the bottom of the well and a bottom face 1026 of the anchor plug 1020. Grooves 1013 are provided that extend from the transverse bore 1012 to a top surface 1016 of the anchor body 1010, to allow for movement of a suture through the anchor body 1010 when the anchor body 1010 is in place in a bone. Therefore, once the anchor body 1010 is driven into a bone or other tissue, with a suture threaded through the transverse bore 1012, the suture is movable in the grooves 1013. The suture may be moved to the desired tension or secured in the suture anchor 1000 by engaging the anchor plug 1020 in the anchor body 1010 and driving the anchor plug 1020 until the plug engages the suture, thereby preventing movement of the suture. The suture is secured between a bottom face 1026 of the anchor plug 1020 and the bottom of the well that is formed in the anchor body 1010.

The anchor plug 1020 may have a head 1024, a threaded post 1023 for engaging the threaded inner surface 1018 of the anchor body 1010, and a bottom face 1026 that is distal to the head 1024. The anchor plug 1020 may also have a bevel 1025 that is complementary to the bevel 1015 of the inner surface 1018. When the anchor plug 1020 is fully engaged in the anchor body 1010, the bevel 1025 is configured to engage the bevel 1015 of the inner surface 1018.

Figure 10:
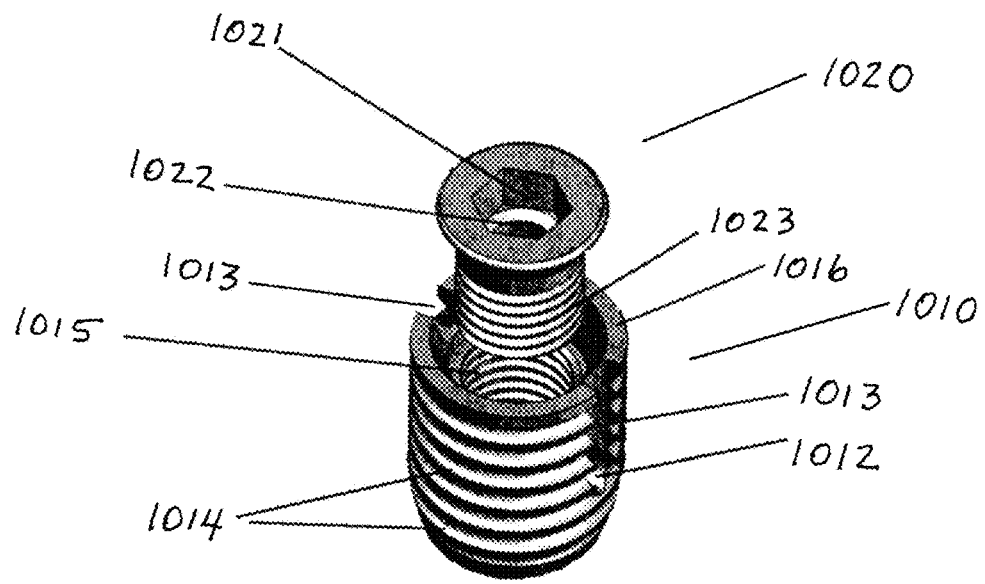
FIG. 10 is a perspective view of a suture anchor, according to one embodiment.
Figure 11:
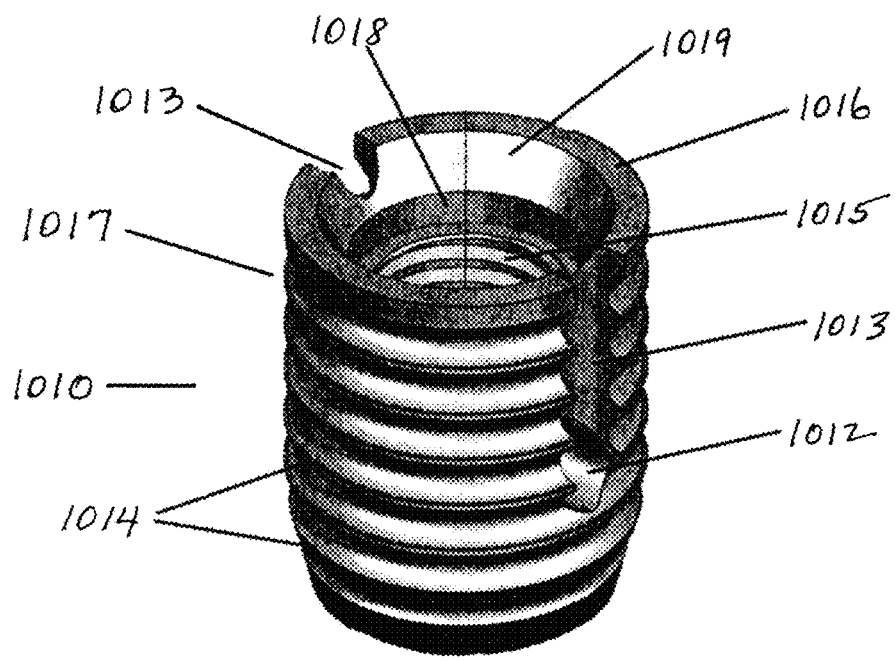
FIG. 11 is a perspective view of an anchor body, according to one embodiment.
Figure 12:
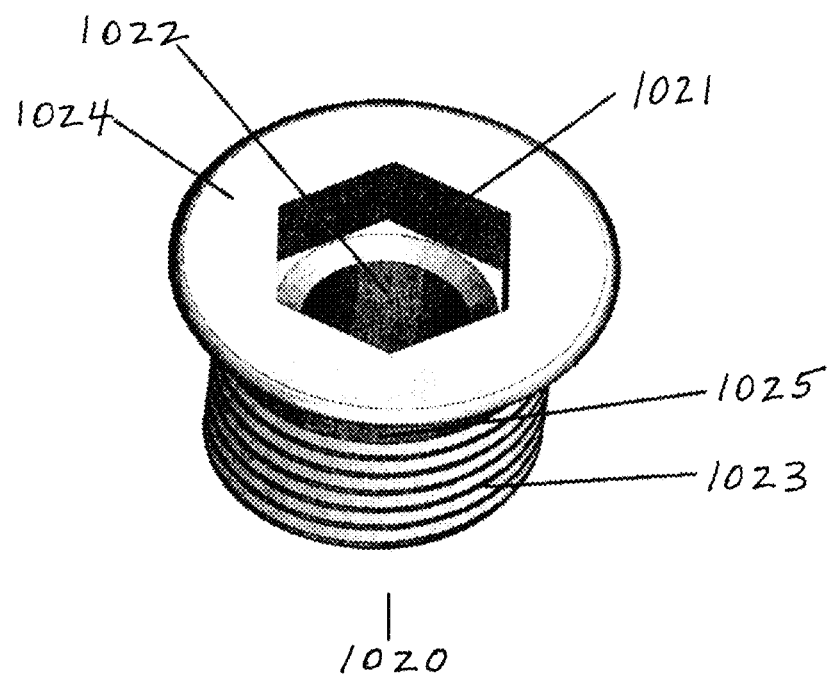
FIG. 12 is a perspective view of an anchor plug, according to one embodiment.
Figure 13:
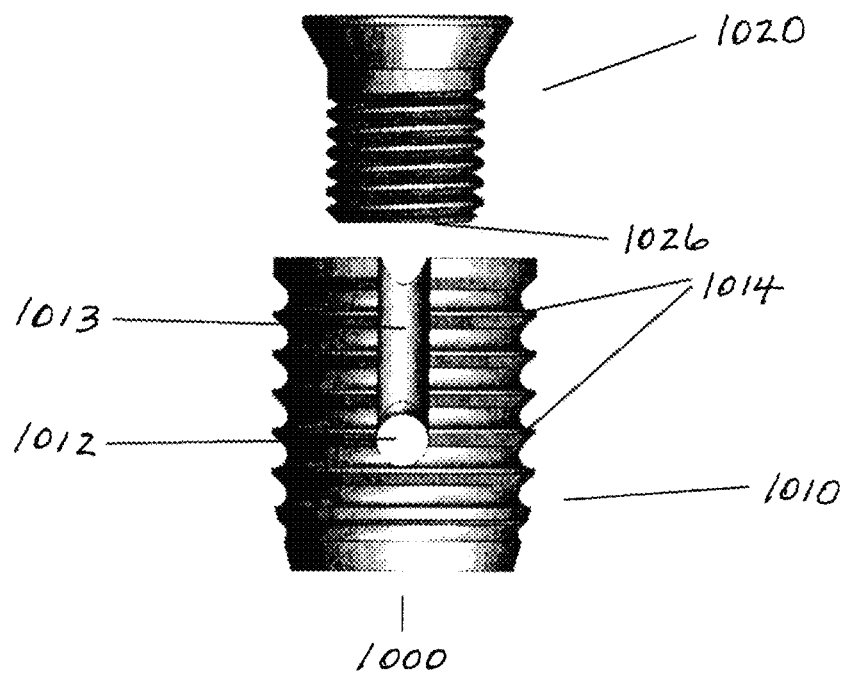
FIG. 13 is a side view of a suture anchor, according to one embodiment.

The anchor plug 1020 may also be configured to be engaged by a complementary driving device such that the anchor plug 1020 may be tightened or loosened in the anchor body 1010. The head 1024 of the anchor plug 1020 is typically shaped or has a recessed area to accommodate engagement with a driving device. For example, the anchor plug 1020 may have a hexagonal drive 1021, as shown in FIGS. 10 and 11, or it may have a slotted drive, a Philips drive, a square drive, a star drive, a nut drive, or other mechanism that is known to those of skill in the art for engaging a complementary drive device. The anchor plug 1020 may be configured such that the top of the head 1024 of the anchor plug 1020 is flush with the top surface 1016 of the anchor body 1010, recessed in the anchor body 1010, or above the anchor body 1010, when the anchor plug 1020 is fully engaged in the anchor body 1010.

Such suture anchors 1000 allow for tightening, adjustment, or re-tensioning of a suture by tightening, loosening, re-tightening, and/or removing the anchor plug 1020 from anchor body 1010. Such suture anchors 1000 also allow for securing of the suture without the tying of knots or replacement of sutures when re-tensioning is required. Suture anchors 1000 may be used for the fixation of soft tissue to bone, or of bone to bone.

Suture anchors 1000 and plugs 1020 may be made from a variety of materials known to those of skill in the art. For example, for the suture anchors 1000 the material is typically a rigid material such as a metal, a polymer, or a ceramic. Biocompatible metals include, but are not limited to stainless steel, titanium, tantalum, aluminum, chromium, molybdenum, cobalt, silver, and gold, or alloys of such metals that are known to those of skill in the art. Biocompatible polymers include, but are not limited to, high-density polyethylenes, polyurethanes, or blends of such polymers, as are known to those of skill in the art. Biocompatible polymers also include absorbable materials such as polylactic acid, polyglycolic acid, or mixtures thereof. Biocompatible ceramics include, but are not limited to alumina, silica, silicon carbide, silicon nitride, zirconia, and mixtures of any two or more thereof.

The plugs 1020 may likewise be prepared from similar metals, polymers, and ceramics, however in some embodiments, the anchor plugs are prepared from materials that may be compressed. In such embodiments, the plug material is capable of being compressed from an uncompressed state to a compressed state, prior to or during insertion of the plug into the anchor body 1010. Such compression allows for the material to recoil from the compressed state to the uncompressed state and thereby increasing the friction fit between the plug and the anchor body 1010. Such materials that may be compressed include, but are not limited to, polyethylenes, silicones, polyesters, polyurethanes, polylactic acid, polyglycolic acid, or mixtures of any two or more thereof.

The anchor 1000 may be used to secure sutures tensioning tissue without direct contact of tissue to bone. Examples of such uses of suture tensioning without tissue to bone contact include, but are not limited to, pelvic surgery, bladder suspension surgery, brow lift or face lift surgery, hand surgery and the like.

Methods of using suture anchors 300, 1000 are also provided. For example, referring to FIGS. 5-8 and 10-13, suture anchor 1000 is capable of adjustably retaining a suture. In a typical procedure, a nest, or hole, is drilled into a bone. The anchor body 1010, is then placed at the top of the nest and inserted such that the transverse bore 1012 is not obscured in the bone. The suture is then threaded through a tissue to be secured, and the ends of the suture are threaded through the transverse bore 1012. The anchor body 1010 may then be fully or partially driven into the nest, such that the suture is guided by the grooves 1013 and is freely moving through the grooves 1013 and transverse bore 1012. The anchor plug 1020 may then be engaged in the anchor body 1010 and driven into the anchor body 1010 until sutures are nearly engaged. The tension of the suture may then be set by the surgeon, or other medical professional, and the anchor plug 1020 fully engaged to secure the sutures within the suture anchor 1000. To re-adjust the tension of the suture, the anchor plug 1020 may be driven in a reverse direction to loosen the anchor plug 1020, thereby allowing for free movement of the suture and the process of tensioning the suture may be repeated.

Figure 9:
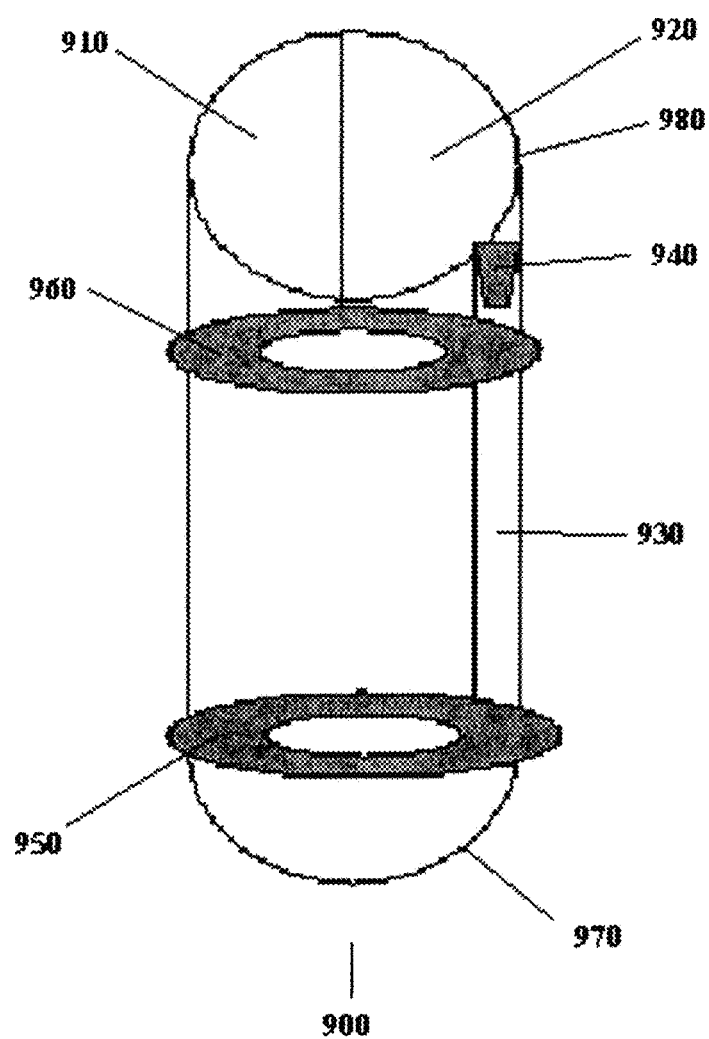
FIG. 9 is a side view of a cannula.

Referring now to FIG. 9, in another aspect, a cannula 900 comprising at least one chamber 910, 920, an air passage 930 having a valve 940, and at least one inflatable donut 950 is described. The cannula 900 has a distal end 970 and a proximal end 980. The inflatable donut 950 is located at, or near the distal end 970 of the cannula 900. The cannula may be used in both arthroscopic and endoscopic surgery. The cannula may be used to facilitate the passage of surgical items such as but not limited to instruments, sutures, and implants, into and out of a subject. The cannula 900 may be at least a single chambered passageway or the cannula 900 may be divided into multiple chambers, such as two chambers 910, 920 as illustrated in FIG. 9, or more than two chambers, depending upon the intended use of the cannula for a given procedure or procedures. In some embodiments, a flexible diaphragm is used to divide cannula 900 into multiple chambers 910, 920. In some such embodiments, the flexible diaphragm extends the entire length of the cannula 900. The donut 950 is an inflatable donut that, when inflated, has a larger diameter than a diameter of the cannula 900. Cannula 900 may also comprise a second donut 960, that may be rigid or inflatable. The second donut 960 may be located at or near the proximal end 980. In one aspect, the cannula 900 is inserted through the skin of a subject and the donut 950 is inflated via the air passage 930. In one embodiment, inflation of donut 950 is via a pump connected to the valve 940, and subsequent filling of the air chamber 930 and donut 950 with air from the pump. In another embodiment, inflation of donut 950 is via insertion of an air-filled syringe through the valve 940, and subsequent filling of the air chamber 930 and donut 950 with air from the syringe. The valve 940 may comprise rubber(s), silicone(s), or other materials known to those of skill in the art to be useful for the insertion and removal of syringes or other devices that may be used for inflation of donut 950. Other methods of inflating the donut 950 will be readily apparent to those of skill in the art. Inflation of donut 950 prevents inadvertent removal of the cannula from the subject during surgical procedures. The presence of inflatable donut 950 allows for less trauma to an insertion point in the skin of a subject by allowing for a cannula 900 of small diameter to be inserted, but then the larger diameter donut 950 prevents removal. In embodiments where the second donut 960 is present, the second donut 960 prevents the inadvertent full insertion of the cannula into a subject beyond the surface of the skin of the subject. As noted above, because the second donut 960 does not pass through the skin of a subject, the second donut may be made of a rigid material or the second donut 960 may be inflatable. The second donut 960 may be integrally formed with cannula 900 or it may be formed separately and attached to cannula 900. In embodiments, where both the first donut 950 and the second donut 960 are inflatable, the donuts 950, 960 may be simultaneously inflatable in a "dumbbell" formation allowing for the inflation both within, via the first donut 950, and external, 960, to the body together.

Generally, cannulas are used to enter areas within the body such as the shoulder, knee or abdomen. Cannulas are also used as a channel to introduce surgical implements such as surgical instruments, suture anchors, or sutures. The cannulas embodied herein allow for separate chambers which allow multiple instruments or items to be entered into the joint but partitioned from one another. Another feature is an expandable, inflatable device on the end of the cannula which prevents expulsion of the cannula from the cavity as intracavitary pressure increases. The inflatable device, i.e. inflatable donut, locks the cannula in place.

In another aspect, methods for using instruments described herein, are provided. For example in some embodiments, methods are disclosed for using the suture passer 100, suture anchor 300, and cannula 900 are described. The embodied methods allow for tissue repair. In some embodiments, the methods provided allow for arthroscopic rotator cuff repair, by attempting to recreate the true native footprint of the rotator cuff of a subject. In some embodiments, such methods comprise preparing the rotator cuff bed, boring a tunnel 510 (FIGS. 5-8), or hole, through a portion of bone such as a humerus 520, passing a suture 530 through the tunnel 510, suturing the tissue using a suture passer 100, and anchoring the sutures 530 in the suture anchor 300, thereby securing the rotator cuff muscles to the bone In some embodiments of the methods, the suture passer 100 descends through one chamber 950, 960 of the cannula 900, grasping tissue. The suture passer 100 passes a locking stitch as described above, followed by removal of the suture passer 100, with the sutures remaining in the chamber 950, 960 of the cannula 900. The other chamber 950, 960 of the cannula 900 has a humerus drill inserted. A small hole is bored in a greater tuberosity. One limb of a suture is then passed through the bone. A suture anchor 300 is then placed into the greater tuberosity. Sutures may be placed through the suture anchor 300 either before or after insertion. If not previously completed, the suture anchor 300 is then fixated in the bone. The sutures are then tensioned thus tensioning the tissue. The plug 320 of the suture anchor 300 is then engaged in the anchor 310 and locked into position, thus securing the sutures. This step can be repeated to alter the tension of the sutures and therefore re-tensioning the sutures and tissue.

For the purposes of this disclosure and unless otherwise specified, "a" or "an" means "one or more."

One skilled in the art will readily realize that all ranges discussed can and do necessarily also describe all subranges therein for all purposes, and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

While some embodiments have been illustrated and described, it should be understood that changes and modifications can be made therein in accordance with ordinary skill in the art without departing from the invention in its broader aspects as defined in the following claims.

What is claimed is:

1. A tissue anchor comprising: an anchor body comprising:
   a body outer surface, a body inner surface, a top surface, and a bottom inner surface and a bottom outer surface distal to the top surface;
   the body inner surface and the bottom inner surface defining a well;
   the body inner surface having a distal portion and a proximal portion, the distal portion having a threaded region and the proximal portion having a non-threaded surface, the proximal portion having a cross-sectional dimension larger than a largest cross-sectional dimension of the threaded region of the distal portion; and
   a transverse bore extending through the anchor body proximal of the bottom inner surface; and
   an anchor plug configured to be received by the well, the anchor plug comprising:
   a distal bottom surface;
   a proximal top surface;
   a distal portion; and
   a proximal portion;
   wherein the transverse bore is capable of receiving one or more sutures to be secured between the bottom inner surface of the well and the distal bottom surface of the anchor plug.

2. The tissue anchor of claim 1, wherein the proximal portion of the anchor plug extends from the proximal top surface, the proximal portion of the anchor plug having a larger diameter than the distal portion of the anchor plug, the proximal portion of the anchor plug being sized for receipt of the proximal top surface of the anchor plug in the proximal portion of the body inner surface of the anchor body.

3. The tissue anchor of claim 1, wherein the body outer surface comprises bone engaging features along a majority of a length of the body outer surface.

4. The tissue anchor of claim 3, wherein the bone engaging features comprise ridges or rungs.

5. The tissue anchor of claim 1, further comprising one or more sutures received through the transverse bore.

6. The tissue anchor of claim 1, wherein the transverse bore comprises a pair of opposed transverse openings extending through the anchor body from the body outer surface to the body inner surface proximal of the bottom inner surface.

7. The tissue anchor of claim 6, further comprising one or more sutures received through the pair of opposed transverse openings.

8. The tissue anchor of claim 1, wherein the distal portion of the body inner surface has a region of constant diameter along a longitudinal extent of the anchor body, the proximal portion having a larger diameter than the distal portion.

9. The tissue anchor of claim 1, wherein the body outer surface comprises rungs.

10. The tissue anchor of claim 1, further comprising grooves in the body outer surface aligned with ends of the transverse bore.

11. The tissue anchor of claim 10, wherein the grooves extend from the transverse bore to the top surface.

12. The tissue anchor of claim 1, wherein the anchor plug includes a threaded outer surface.

13. The tissue anchor of claim 1, wherein the anchor plug is removable from the anchor body in order to allow the one or more sutures secured by the tissue anchor to be re-tensioned.

14. The tissue anchor of claim 1, wherein the anchor plug includes threads extending to a distal end of the anchor plug.

15. The tissue anchor of claim 1, wherein the anchor plug includes a threaded region and a region proximal of the threaded region having a non-uniform outer circumference.

16. The tissue anchor of claim 1, wherein the body outer surface comprises ridges.

17. A tissue anchor comprising:
an anchor body comprising:
a body outer surface with bone engaging features extending outwardly therefrom along a majority of a length of the body outer surface;
a body inner surface having threads;
a bottom inner surface and a bottom outer surface, the body inner surface and the bottom inner surface defining a well; and
a pair of opposed transverse openings extending through the anchor body from the body outer surface to the body inner surface proximal of the bottom inner surface; and
an anchor plug configured to be received by the well and having threads to threadingly engage the threads of the body inner surface, the anchor plug threads extending to a distal end of the anchor plug, the anchor plug including a bottom surface;
wherein the pair of opposed transverse openings are configured to receive one or more sutures to be secured between the bottom inner surface of the well and the bottom surface of the anchor plug.

18. The tissue anchor of claim 17, further comprising grooves in the body outer surface aligned with ends of the transverse bore.

19. The tissue anchor of claim 18, wherein the grooves extend from the transverse bore to a top surface of the anchor body.

20. The tissue anchor of claim 17, wherein the anchor plug is removable from the anchor body in order to allow the one or more sutures secured by the tissue anchor to be re-tensioned.

21. The tissue anchor of claim 17, wherein the bone engaging features comprise ridges or rungs.

22. The tissue anchor of claim 21, wherein the bone engaging features comprise ridges.

23. The tissue anchor of claim 21, wherein the bone engaging features comprise rungs.

* * * * *